US00PP12821P2

(12) United States Plant Patent
Booman

(10) Patent No.: US PP12,821 P2
(45) Date of Patent: Aug. 6, 2002

(54) SARRACENIA PLANT NAMED 'COBRA NEST'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 61 days.

(21) Appl. No.: 09/774,365

(22) Filed: Feb. 1, 2001

(51) Int. Cl.[7] ..... A01H 5/00

(52) U.S. Cl. ..... Plt./263

(58) Field of Search ..... Plt./263, 373

*Primary Examiner*—Bruce R. Campell
*Assistant Examiner*—Wendy A Baker
(74) *Attorney, Agent, or Firm*—C. A. Whealy

(57) ABSTRACT

A new and distinct cultivar of Sarracenia plant named 'Cobra Nest' characterized by its compact and dense plants with numerous leaves; relatively rapid growth rate; and upright, stong and burgundy-colored leaves with large undulating lids.

1 Drawing Sheet

BACKGROUND OF THE INVENTION

The present Invention relates to a new and distinct cultivar of Sarracenia, botanically known as *Sarracenia hybrida*, and hereinafter referred to by the cultivar name 'Cobra Nest'.

The new Sarracenia was discovered by the Inventor as a seedling originating from a cross of two unidentified selections of *Sarracenia hybrida*, not patented. The cultivar Cobra Nest was discovered and selected by the Inventor as a single plant within the progeny of the stated cross in a controlled environment in Vista, Calif.

Asexual reproduction of the new Sarracenia by tissue-culture propagation in a laboratory in Rancho Sante Fe, Calif., since Spring, 1998, has shown that the unique features of this new Sarracenia are stable and reproduced true to type in successive generations.

SUMMARY OF THE INVENTION

The new Sarracenia has not been observed under all possible environmental conditions. The phenotype may vary somewhat with variations in environment such as temperature, daylength, light intensity, relative humidity, nutritional and water status without, however, any variance in genotype.

The following traits have been repeatedly observed and are determined to be the unique characteristics of 'Cobra Nest'. These characteristics in combination distinguish 'Cobra Nest' as a new and distinct cultivar:

1. Compact and dense plants with numerous leaves.

2. Relatively rapid growth rate.

3. Upright, strong and burgundy-colored leaves with large undulating lids.

Plants of the new Sarracenia can be compared to plants of the parental selections, the unidentified selections of *Sarracenia hybrida*. In side-by-side comparisons conducted by the Inventor in Vista, Calif., plants of the new Sarracenia differed from plants of the unidentified selections of *Sarracenia hybrida* in the following characteristics:

1. Plants of the new Sarracenia are more dense and have more leaves per plant than plants of the unidentified selections of *Sarracenia hybrida*.

2. Plants of the new Sarracenia are faster growing and more vigorous than plants of the unidentified selections of *Sarracenia hybrida*.

3. Leaves of the new Sarracenia are more burgundy red in color than plants of the unidentified selections of *Sarracenia hybrida*.

4. Due to its larger size and forward arching angle of the leaf lid, leaves of plants of the new Sarracenia do not collapse when watered from overhead whereas leaves of the unidentified selections tend to collapse when watered from overhead as plants of the unidentified selections have smaller and more open lids that do not keep water from entering the leaf tube.

Plants of the new Sarracenia can be compared to plants of an unidentified selection of *Sarracenia flava*. In side-by-side comparisons conducted by the Inventor in Vista, Calif., plants of the new Sarracenia differed from plants of the unidentified selection of *Sarracenia flava* in the following characteristics:

1. Plants of the new Sarracenia are more compact and have more leaves per plant than plants of the unidentified selection of *Sarracenia flava*.

2. Plants of the new Sarracenia have shorter leaves than plants of the unidentified selection of *Sarracenia flava*.

3. Leaves of the new Sarracenia are more burgundy red in color than leaves of the unidentified selection of *Sarracenia flava*.

4. Due to its larger size and forward arching angle of the leaf lid, leaves of plants of the new Sarracenia do not collapse when watered from overhead whereas leaves of the unidentified selections tend to collapse when watered from overhead as plants of the unidentified selection of *Sarracenia flava* have smaller and more open lids that do not keep water from entering the leaf tube.

Plants of the new Sarracenia can also be compared to plants of an unidentified selection of *Sarracenia rubra*. In side-by-side comparisons conducted by the Inventor in Vista, Calif., plants of the new Sarracenia differed from plants of the unidentified selection of *Sarracenia rubra* in the following characteristics:

1. Plants of the new Sarracenia are more vigorous than plants of the unidentified selection of *Sarracenia rubra*.

2. Plants of the new Sarracenia have larger and wider leaves than plants of the unidentified selection of *Sarracenia rubra*.

BRIEF DESCRIPTION OF THE PHOTOGRAPH

The accompanying colored photograph illustrates the overall appearance of the new Sarracenia. This photograph shows the colors as true as it is reasonably possible to obtain in colored reproductions of this type. Colors in the photograph may differ slightly from the color values cited in the detailed botanical description which accurately describe the colors of the new Sarracenia. The photograph comprises a side perspective view of a typical plant of 'Cobra Nest'.

DETAILED BOTANICAL DESCRIPTION

The aforementioned and following observations, measurements and values describe plants grown in a polyethylene-covered greenhouse in Vista, Calif., during the spring and summer under conditions which approximate commercial production practices. After the tissue-cultured plants were rooted, the plants were planted in 10-cm containers and grown with day temperatures ranging from 18 to 43° C., night temperatures ranging from 13 to 21° C., light levels about 3,000 foot-candles, and relative humidity levels higher than 55%. Plants used for the following description were about 3 to 4 months old from a rooted tissue-cultured plantlet. In the following description, color references are made to The Royal Horticultural Society Colour Chart except where general terms of ordinary dictionary significance are used.

Botanical classification: *Sarracenia hybrida* cultivar Cobra Nest.

Parentage: Seedling from a cross between two unidentified selections of *Sarracenia hybrida*, not patented.

Propagation:

*Type.*—By tissue culture.

*Time to initiate roots on a tissue-culture plantlet.*—About 35 days at 21° C.

*Time to develop roots on a tissue-cultured plantlet.*—About 42 days at 28° C.

*Root description.*—Thick, freely branching, white in color.

Plant description:

*Plant growth habit.*—Rosette; compact; full and dense; upright carnivorous perennial plant with numerous erect and strong leaves. Relatively rapid growth rate and relatively vigorous. Suitable for 10-cm containers.

*Plant height, soil level to top of leaves.*—About 17.7 cm.

*Plant width.*—About 23 cm.

Foliage description:

*Shape.*—Tubular to trumpet-shaped, slender at base and swollen at apex; mostly erect; keel on one side of leaf; large terminal lid; sessile. Lid, forward arching; hemispherical in shape; apex rounded; margin, entire and undulating.

*Number of leaves per plant.*—About 30.

*Leaf length.*—About 17.7 cm.

*Leaf diameter.*—Apex: About 2.7 cm. Base: About 5 mm.

*Keel length.*—About 17.4 cm.

*Keel diameter.*—About 1.25 cm.

*Lid length.*—About 4 cm.

*Lid width.*—About 5.3 cm.

*Leaf texture.*—Outer surface: Velvety with fine pubescence. Inner surface: Mostly smooth with fine pubescence. Lid: Both surfaces with fine pubescence.

*Color.*—Young leaves, outer surface: 144A; venation, 183A to 187A. Young leaves, inner surface: 144A to 144B. Fully developed leaves, outer surface: Mostly 183A to 187A with green, 144A, undertones; venation, 183A to 187A. Fully developed leaves, inner surface: 144A.

Flower description:

*Flower type and habit.*—Flowers roughly campanulate, pendulous and drooping; single; terminal. Flowers not persistent. Flowers not fragrant.

*Natural flowering season.*—Spring and summer in the U.S.; flowering sporadic; about 2 to 3 flowers per plant.

*Flower longevity on the plant.*—About 4 to 7 days.

*Flower size.*—Diameter: About 6.5 cm. Height: About 2.4 cm.

*Flower buds.*—Length: About 2.5 cm. Diameter: About 2.8 cm. Shape: Roughly spherical. Color: 144A to 144B.

*Petals.*—Arrangement/appearance: Single whorl of five petals. Length: About 4.1 cm. Width: About 2 cm. Shape: Roughly spatulate; apex, obtuse; base, obtuse. Margin: Entire. Texture: Smooth, glabrous; velvety. Color: Upper surface: 144C to 144D faintly overlain with 59B. Lower surface: 144C to 144D overlain with 59B.

*Sepals.*—Arrangement/appearance: Single whorl of five sepals; calyx, star-shaped. Length: About 3.3 cm. Width: About 2.3 cm. Shape: Ovate; apex, obtuse; base, obtuse with truncate tendencies. Margin: Entire. Texture: Smooth, glabrous. Color: Upper surface: 144D; margin, 183A. Lower surface: 144B to 144C; margin, 183A.

*Bracts.*—Arrangement/apearance: Single whorl of three bracts appressed to sepals. Length: About 1 cm. Width: About 8 mm. Shape: Deltoid; apex, acute; base, obtuse. Margin: Entire. Texture: Smooth, glabrous. Color, both surfaces: 144A to 144B.

*Scapes.*—Length: About 12 cm. Diameter: About 3 mm. Strength: Moderately strong, flexible. Angle: Towards base, erect; towards apex, bent. Texture: Smooth, glabrous. Color: 144A overlain with 183A to 187A.

*Reproductive organs.*—Stamens: Quantity: Five per flower. Filament length: About 9 mm. Filament color: White, closest to 155D. Anther shape: Oblong. Anther length: About 3 mm. Anther color: 14A. Pollen: None observed to date. Pistils: Quantity: One per flower. Pistil length: About 2.2 cm. Style appearance: Style expanded at the apex into a fleshy umbrella-like cap. Diameter of cap: About 3.6 cm. Height of cap: About 2 cm. Color, both surfaces: 144D. Ovary arrangement: Superior. Ovary color: 144D to 154A.

*Seeds.*—Seed development has not been observed to date.

Disease resistance: Plants of the new Sarracenia have not been noted to be resistant to pathogens common to Sarracenias. Plants of the new Sarracenia have not been noted to be susceptible to pathogens common to Sarracenias.

Temperature tolerance: Plants of the new Sarracenia tolerate temperatues ranging from 0° to greater than 43° C.

It is claimed:

1. A new and distinct Sarracenia plant named 'Cobra Nest' as illustrated and described.

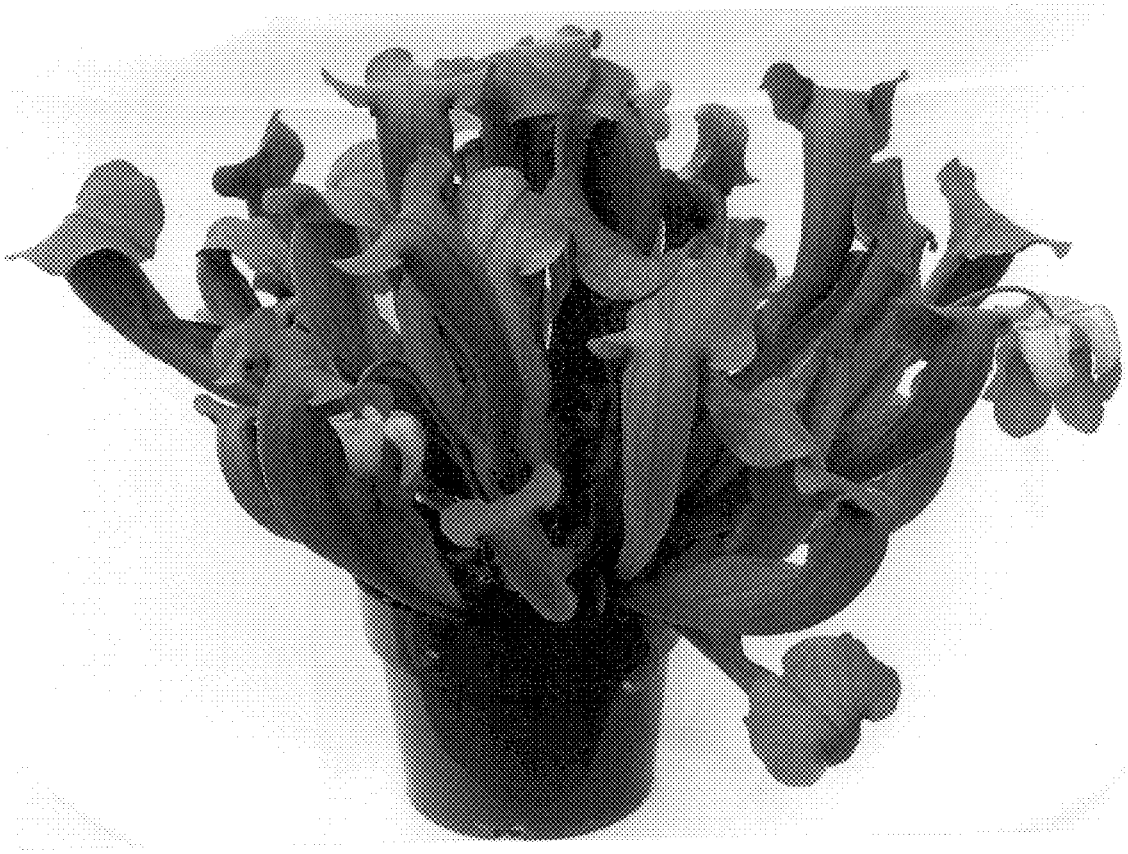

* * * * *